United States Patent
Dewaele et al.

(10) Patent No.: US 9,622,729 B2
(45) Date of Patent: Apr. 18, 2017

(54) CROSSTALK REDUCING HANDLE FOR SURGICAL ARTICULATED INSTRUMENTS

(71) Applicant: STEERABLE INSTRUMENTS BVBA, Sint-Denijs-Westrem (BE)

(72) Inventors: Frank Dewaele, De Pinte (BE); Bart Blanckaert, Eeklo (BE); Cyriel Mabilde, Oudenaarde (BE)

(73) Assignee: Steerable Instruments NV, Sint-Denijs-Westrem (BE)

( * ) Notice: Subject to any disclaimer, the term of this patent is extended or adjusted under 35 U.S.C. 154(b) by 0 days.

(21) Appl. No.: 14/433,093

(22) PCT Filed: Oct. 4, 2013

(86) PCT No.: PCT/EP2013/070745
§ 371 (c)(1),
(2) Date: Apr. 2, 2015

(87) PCT Pub. No.: WO2014/053652
PCT Pub. Date: Apr. 10, 2014

(65) Prior Publication Data
US 2015/0265262 A1   Sep. 24, 2015

Related U.S. Application Data

(60) Provisional application No. 61/712,334, filed on Oct. 11, 2012.

(30) Foreign Application Priority Data

Oct. 6, 2012 (EP) ..................... 12187552

(51) Int. Cl.
*A61B 17/00* (2006.01)
*A61B 17/29* (2006.01)

(52) U.S. Cl.
CPC .... *A61B 17/00234* (2013.01); *A61B 17/2909* (2013.01); *A61B 2017/003* (2013.01);
(Continued)

(58) Field of Classification Search
CPC ....... A61B 17/32; A61B 17/29; A61B 17/115; A61B 17/125; A61B 17/28; A61B 17/00
(Continued)

(56) References Cited

U.S. PATENT DOCUMENTS 5,275,608 A * 1/1994 Forman .................. A61B 17/29
606/170
5,395,367 A * 3/1995 Wilk ................ A61B 17/00234
606/1

(Continued)

FOREIGN PATENT DOCUMENTS

GB       2421912 A      7/2006
WO    2010002904 A1    1/2010

OTHER PUBLICATIONS

PCT Notification Concerning Transmittal of International Preliminary Report on Patentability and Written Opinion of the International Searching Authority dated Apr. 7, 2015 in connection with PCT International Patent Application No. PCT/EP2013/070745, 5 pages.

*Primary Examiner* — William Thomson
*Assistant Examiner* — Victor Shapiro
(74) *Attorney, Agent, or Firm* — Amster, Rothstein & Ebenstein LLP

(57) ABSTRACT

The present invention relates to a bodily invasive steerable device (100) having a proximal (201) and distal (205) end comprising a steering mechanism (50) having a proximal bending part (202), a distal bending part (204), and an intermediate part (203) disposed between the proximal bending part (202) and the distal bending part (204) con-
(Continued)

figured mechanically to transmit forces applied at the proximal end (201) to the distal end (205). The steering is mechanism configured such that the distal bending part (204) moves responsive to movements of the proximal bending part (202). The device also comprises a handle (206) coupled to the proximal bending part (202) to effect manual bending. The handle (206) comprises at least one grip member (210) that extends distally (205), at least over the proximal terminal end (171) of the proximal bending part (202).

11 Claims, 19 Drawing Sheets

(52) U.S. Cl.
CPC ........... *A61B 2017/0042* (2013.01); *A61B 2017/0069* (2013.01); *A61B 2017/00305* (2013.01); *A61B 2017/00314* (2013.01); *A61B 2017/00424* (2013.01); *A61B 2017/291* (2013.01); *A61B 2017/2908* (2013.01); *A61B 2017/2927* (2013.01)

(58) Field of Classification Search
USPC ...... 606/170, 205, 139, 1; 600/564; 604/528
See application file for complete search history.

(56) References Cited

U.S. PATENT DOCUMENTS

| | | | | |
|---|---|---|---|---|
| 5,766,196 | A * | 6/1998 | Griffiths | A61B 17/29 600/564 |
| 7,338,513 | B2 * | 3/2008 | Lee | A61B 17/29 606/139 |
| 7,615,067 | B2 * | 11/2009 | Lee | A61B 17/29 604/528 |
| 2003/0109898 | A1 | 6/2003 | Schwarz et al. | |

* cited by examiner

PRIOR ART

PRIOR ART
FIG. 4
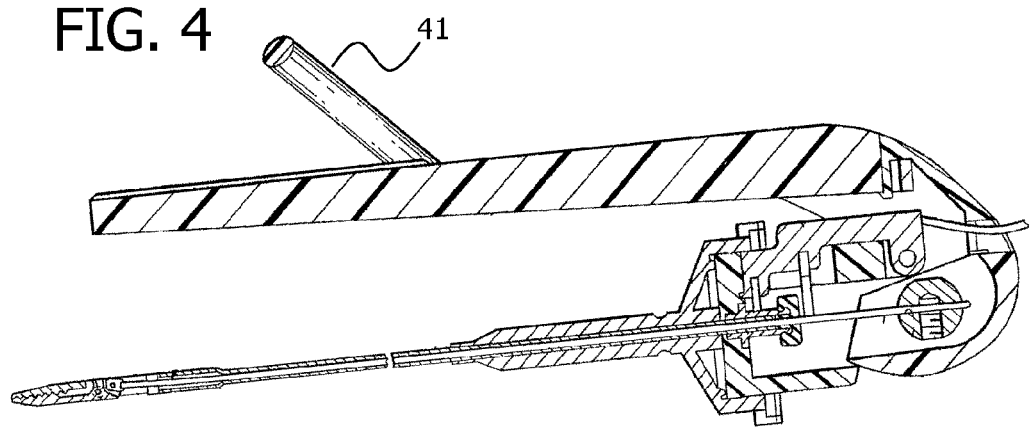
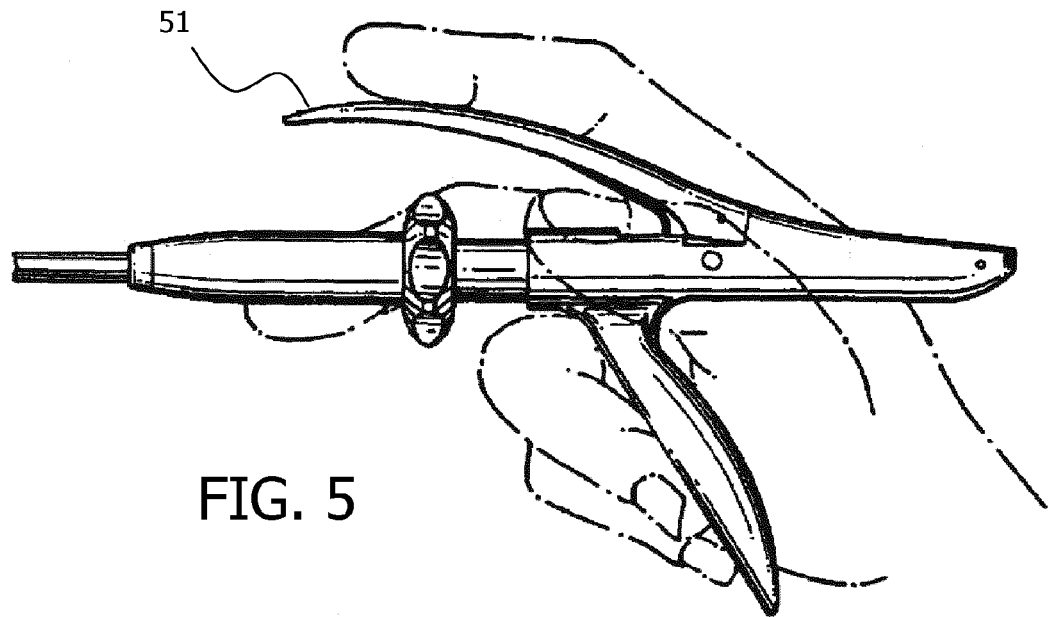
FIG. 5

PRIOR ART

PRIOR ART

PRIOR ART

PRIOR ART
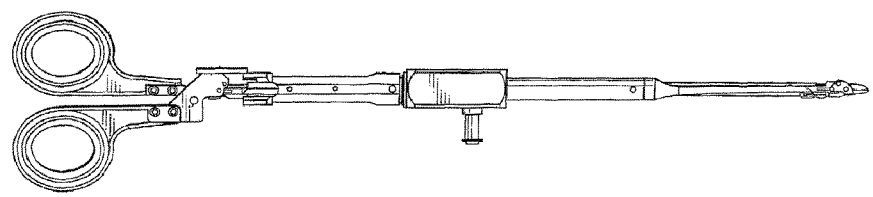
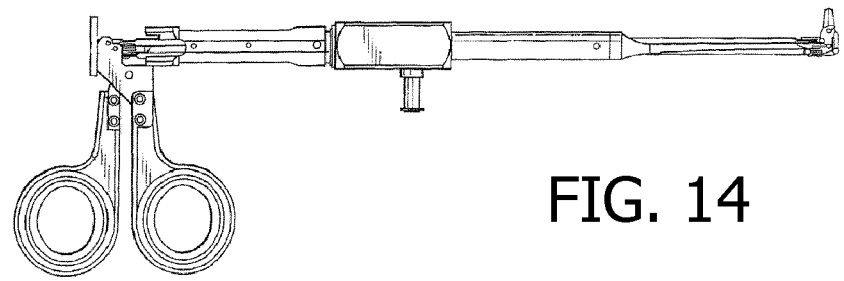
FIG. 14
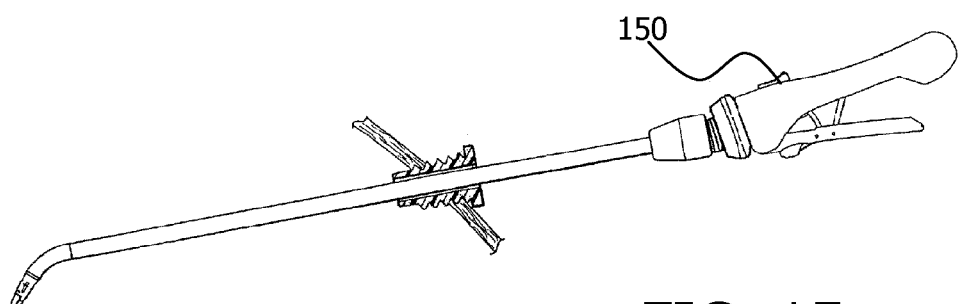
FIG. 15

PRIOR ART
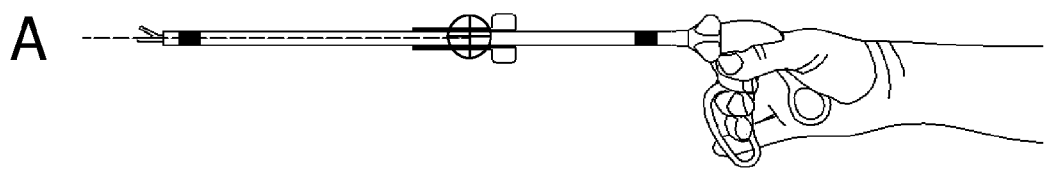
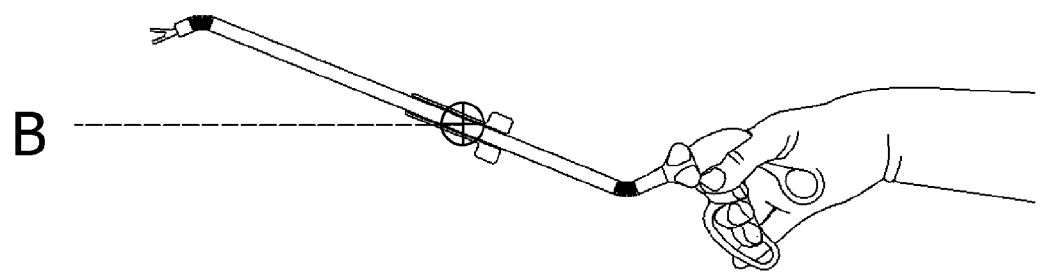
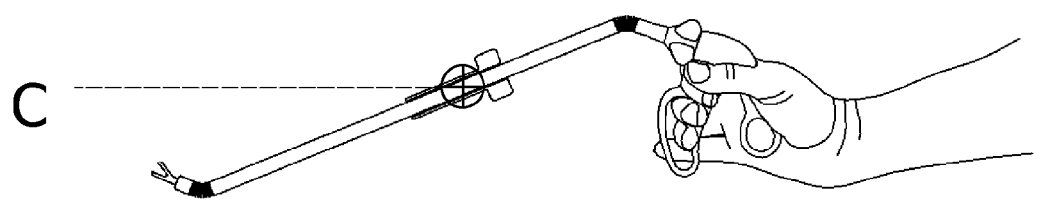
FIG. 22

CROSSTALK REDUCING HANDLE FOR SURGICAL ARTICULATED INSTRUMENTS

CROSS-REFERENCE TO RELATED APPLICATIONS

This application is a U.S. national stage application under 35 U.S.C. §371 of PCT International Patent Application No. PCT/EP2013/070745, filed Oct. 4, 2013, which claims priority to European Patent Application No. 12187552.0, filed Oct. 6, 2012 and U.S. Provisional Patent Application No. 61/712,334, filed Oct. 11, 2012, the contents of all of which are herein incorporated by reference in their entirety.

FIELD OF THE INVENTION

The invention relates to a handle for articulated instruments or videoscopes having enhanced control, which can be used in high-precision or medical applications.

BACKGROUND OF THE INVENTION

Surgery is characterized by a continuous search towards minimal invasiveness.

Since the 1980s open surgery is largely replaced by an endoscopic approach in which long instruments are inserted through trocars in a $CO_2$ extended abdomen.

Laparoscopic surgery, known for its validated benefits of shorter hospitalization, less postoperative pain and earlier recovery, is more demanding for the surgeon.

Precise dissection, suturing and knot tying in minimal access surgery is an advanced skill. Especially when the suture line and the axis of the needle holder are unparallel this skill is difficult to master.

Recent steps in the evolution towards minimal invasiveness are Single Port Surgery (SPS) and Natural Orifice Transluminal Endoscopic Surgery (NOTES). Both approaches result in a scarless healing. In SPS the instruments are inserted through one big trocar through e.g. the umbillicus. NOTES is a surgical technique whereby abdominal operations are performed with an endoscope passed through a natural orifice e.g. mouth through an internal incision in the stomach, bladder or colon. In these procedures surgery is made more challenging by the spatial constraints and the lack of triangulation.

A disadvantage of endoscopic surgery is reduced dexterity for the surgeon. This is mainly because of the fulcrum effect and the absence of wrist like movements at the tip of the instrument. Awareness of this disadvantage increases as more complex endoscopic procedures and single port surgeries (characterized by sword fighting of the instruments) are performed.

The fulcrum effect is explained by the long instruments that pivot at the level of the trocar inserted in the abdomen. A movement of the handle to the left is translated in a movement to the right at the effector (e.g. a pair of scissors). It is surprising to see how fast surgeons adapt to these inversed movements.

The lack of wrist-like movements is more difficult to overcome. A state-of-the-art solution is provided by the Da Vinci robot (Intuitive Surgical). In this master slave system all the movements of the surgeons' hands at the console are transferred to fluent movements at the instruments' tip. This solution is quite expensive, leading to the development of cheaper hand instruments with an omni-directional articulated tip.

Most of the challenge is explained by the reduced dexterity. A conventional rigid laparoscopic instrument offers only 4 degrees of freedom (rotation, up/down angulations, left/right angulations, in/out movements).

To overcome this restriction in movements, various designs for steerable instruments have been developed:

1. In its simplest form an articulated instruments consist of a prebent flexible tube sliding out of a rigid straight tube (uni-directional articulated instruments). This tip can only bend in one direction and cannot withstand an appropriate amount of lateral force. In another solution the instrument tip is operated via gear trains FIG. 9.

2. More advanced alternatives are instruments that allow bending movements of the tip in one plane e.g. left to right and vice versa FIG. 8-10. Because of the nature of the construction, a mostly stable tip is created. These bi-directional instruments need to be navigated to a point of interest by bending into one direction and then by turning the whole instrument around its own axis. This is not intuitive.

3. True wrist movements are only possible with omni-directional systems FIG. 11-17. The omnidirectional articulated instruments consist mainly of a proximal and distal end, a proximal and distal bending part and an intermediate part in between. Movement of the proximal end is transferred to a movement at the distal end.

Examples are described in U.S. Pat. No. 7,410,483 FIG. 11 and U.S. Pat. No. 8,105,350 FIG. 15.

Similar to robotic surgery, omni-directional articulated instruments provide 7 degrees of freedom (axial rotation and deflection of the tip in two planes are added to the 4 DOF of conventional rigid instruments). A combination of up/down and left/right movements at the proximal side allows to reach any point at the distal effector side without the need for a rotation around its own axis.

The increased maneuverability is paid back by a serious decrease in tip stability. To solve this, hybrid solutions such as the Kymerax® system (Terumo) and Jaimy® system (EndoControl) compensate by using strong electrical motors to restore the tip stability. In US Patent Application Pub. No.: US 2011/0004157 an alternative solution to provide an appropriate tip stability is presented. The steering mechanism is based on a tubular structure with longitudinal cuts.

Omni-directional articulated instruments offer, in comparison to robotic systems the advantages of low costs and tactile feedback.

Nevertheless all these omni-directional articulated instruments are prone to crosstalk, a conflict of two different movements FIG. 21.

Bending the proximal zone 202, in order to deflect the distal tip of the instrument 205, will result in an additional unintended swinging of the whole instrument around its fulcrum point at the level of the trocar 221 in the abdomen FIG. 21. The distal tip 205 will move to the opposite direction.

In other words, to adjust the direction of the articulated tip 205, the orientation of the surgeon hand needs to be changed. This is possible by a rotation of the surgeons' hand around the surgeons' wrist FIG. 21. However this also results in a movement of the proximal bendable part 202 around the surgeons' wrist. The latter will result in a movement of the whole instrument around the fulcrum at the level of the trocar 221 in the abdomen.

The surgeons' hand movements are thus involved in the position of the articulated tip as well as in the direction of the whole instrument.

A prior art solution to overcome the problem of crosstalk is disclosed in U.S. Pat. No. 8,105,350 FIG. 15. A "locking"

feature 150 to keep the tip of the instrument at a constant angle is used. Once the surgeon has the instrument tip in the desired bent position the angle is locked. Thereafter the instrument is further used as a conventional prebent instrument. This results in a complete loss of intuitive wrist like movements.

A second prior art solution to overcome the problem of crosstalk is the use of thumb-controlled (using a small joystick) instruments FIG. 12 instead of wrist-controlled instruments FIG. 11. This has recently be researched by Linde M. Okken. In Surg Endosc (2012) 26:1977-1985 she advocates that thumb control is more suitable for steerable instruments than wrist control to avoid uncontrolled movements. Mostly an additional "locking" feature is mandatory. The thumb-controlled way of steering an instrument is not intuitive.

The crosstalk is thus the result of a rotation point at the surgeons' wrist 223 laying far proximal from the rotation point at the proximal bending part 222 of the steerable instrument FIG. 20.

The longer the distance between the rotation point at the surgeons' wrist 223 and the rotation point at the proximal bending part 222 of the steerable instrument the more crosstalk.

In standard in-line handles the distance is around 260 mm FIG. 20A, for a standard pistol grip handle 200 mm FIG. 20B.

Accordingly, an object of the present invention is to provide an improved endoscopic surgical instrument in which the distance between the rotation point at the surgeons' wrist 223 and the rotation point at the proximal bending part 222 is reduced in order to reduce crosstalk and thus leading to more intuitive movements and enhanced dexterity.

BRIEF DESCRIPTION OF THE FIGURES

FIG. 4 depicts the prior art configuration of a handle for rigid instruments having a distally extending lever mechanism 41 according to U.S. Pat. No. 5,352,223.

FIG. 5 depicts the prior art configuration of a pistol-grip handle for rigid instruments according to U.S. Pat. No. 5,700,275. The index finger rests on a pivoting handle 51.

FIG. 14 depicts the prior art configuration of a traditional in-line handle for an articulated instruments steerable in 4 discrete directions according to U.S. Pat. No. 7,090,689.

FIG. 15 depicts the prior art U.S. Pat. No. 8,105,350. The handle is disposed with a "locking feature" 150.

FIG. 22 illustrates the result of crosstalk due to a long distance between the rotation point at the surgeons' wrist and the rotation point at the proximal bending part of the steerable instrument in the prior art configuration of a pistol-grip like handle. Bending the proximal part, in order to deflect the tip of the instrument downwards, will result in an additional unintended movement of the whole instrument around its fulcrum point upwards FIG. 22B.

SUMMARY OF THE INVENTION

Figure 1:
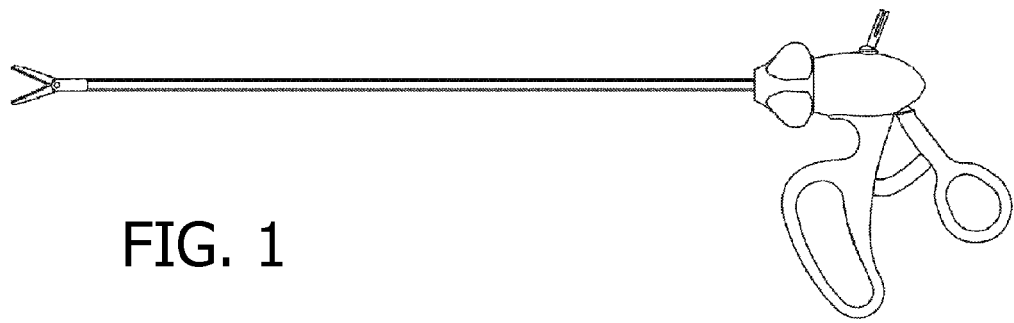
FIG. 1 depicts the prior art configuration of a traditional pistol-grip handle for rigid instruments according to US Patent Application Pub. No.: US 2011/0112366. The ergonomic handle enables a surgeon to use all controls on the instrument, including opening and closing of jaws, rotation and ratcheting them with one hand.
Figure 2:
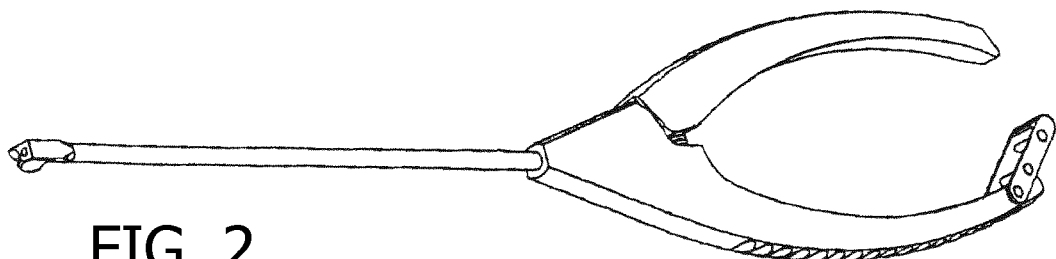
FIG. 2 depicts the prior art configuration of a traditional in-line handle for rigid instruments according to US Patent Application Pub. No.: US 2007/0179524. The handle has a "wishbone" configuration.
Figure 3:
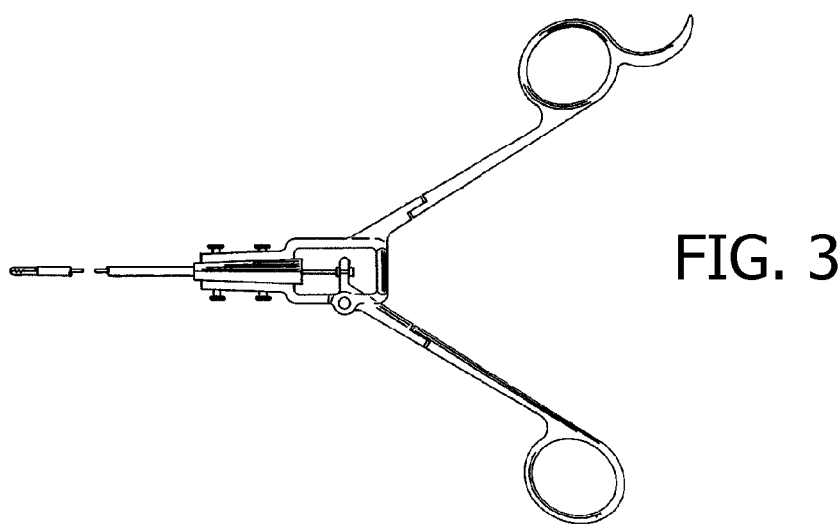
FIG. 3 depicts the prior art configuration of a scissor-style handle for rigid instruments according to U.S. Pat. No. 5,234,460. The proximal end of each handle diverges away from the longitudinal axis of the instrument. The proximal ends of the handles are angled downwardly.
Figure 6:
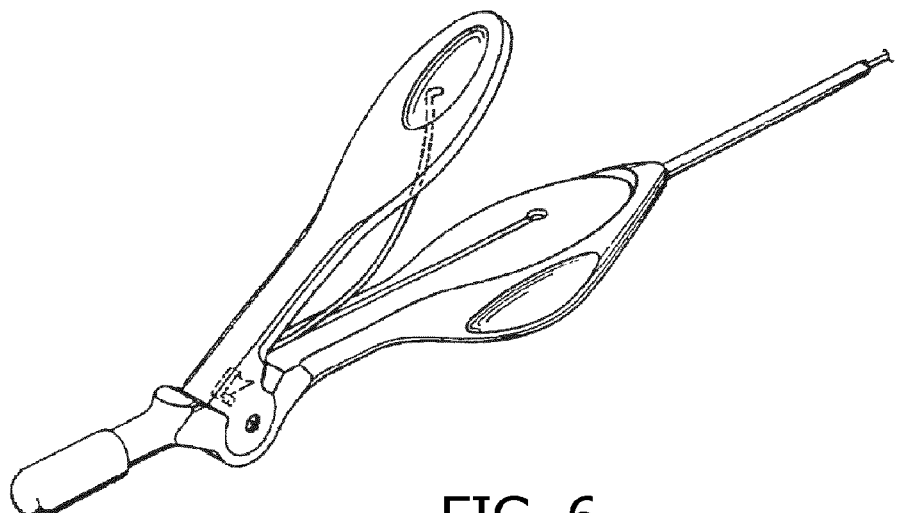
FIG. 6 depicts the prior art configuration of a Snowden Spencer instrument according to U.S. Pat. No. 5,470,328. The instrument is designed to be held in a 'pencil grip' or 'Vardon golf grip' position; both of which are natural gripping relationships between the index finger and opposable thumb. The surgical instrument actually becomes an 'extension' of the surgeon's hand.
Figure 7:
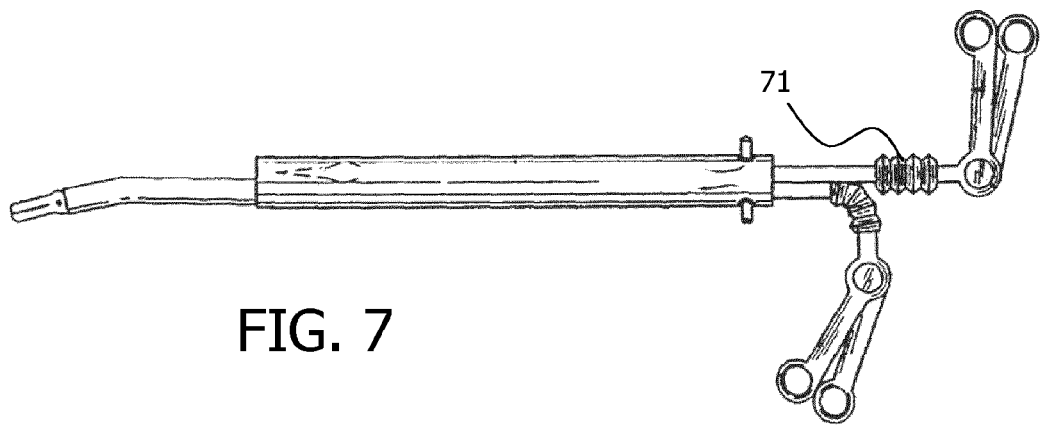
FIG. 7 depicts the prior art configuration for a rigid laparoscopic instrument with a bendable shaft according to U.S. Pat. No. 5,395,367. A connector element (bendable coupling) 71 is provided for connecting the handle to the shaft so that the orientation of the handle with respect to the shaft can be varied prior to the performance of an operation. The bendable shaft section may take the form of a bellows type spring tube as in common use in drinking straws for children.
Figure 8:
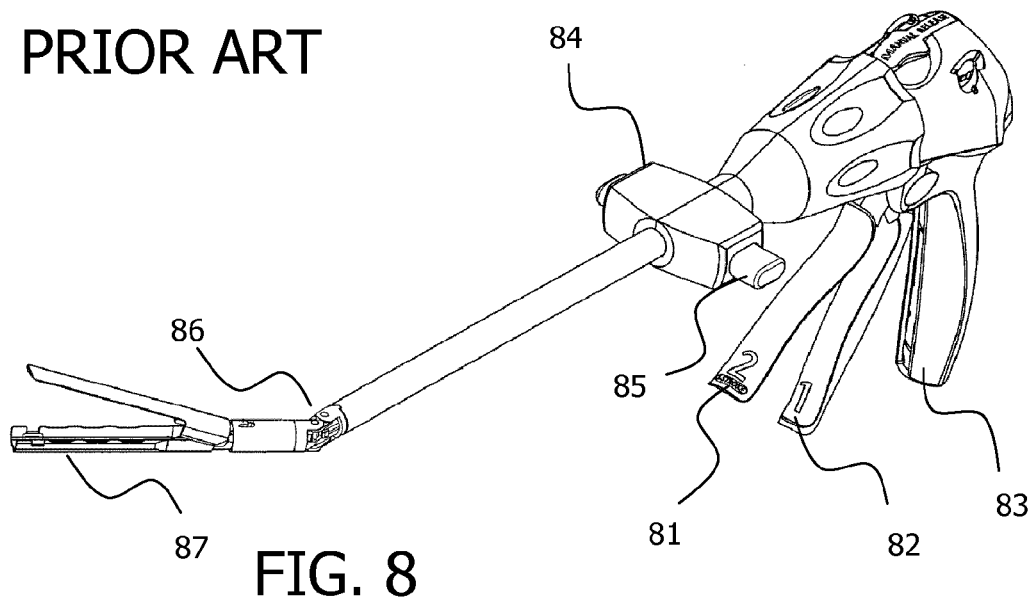
FIG. 8 depicts the prior art configuration of a surgical instrument with a bending articulation controlled articulation pivot joint according to U.S. Pat. No. 7,481,824. The handle portion includes a pistol grip 83 toward which a closure trigger 82 is pivotally and proximally drawn by the clinician to cause clamping or closing of the staple applying assembly 87. A firing trigger 81 is further outboard of the closure trigger and is pivotally drawn by the clinician to cause the stapling of tissue clamped in the staple applying assembly 87. Lateral movement of push buttons 84,85 support the control of the bending articulation mechanism 86.
Figure 9:
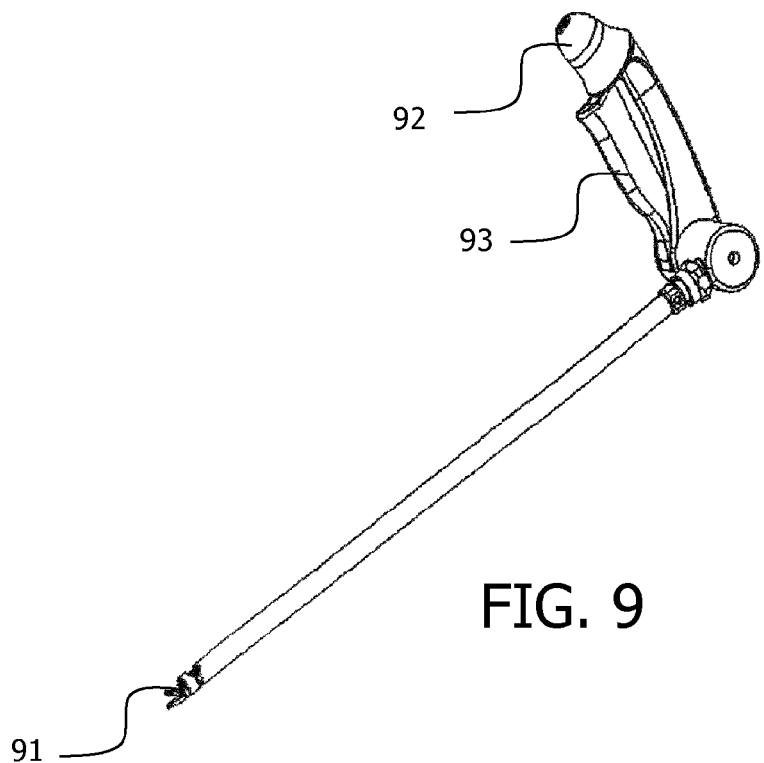
FIG. 9 depicts the prior art configuration of a uni-directional articulated instrument according to US Patent Application Pub. No.: US 2009/0192521. The instrument handle has a number of manipulators and/or operating mechanisms for operating the instrument head and/or effector via gear trains. When actuating the turning knob 92 the motion of rotation thereof is transmitted to the effector 91. The turning knob is operated by the thumb and index. The handle lever 93 actuates the jaws of the effector 91. A forward movement of the handle results in an initial upward movement of the tip (90°) followed by a movement towards the shaft and eventually parallel to the shaft (90°).
Figure 10:
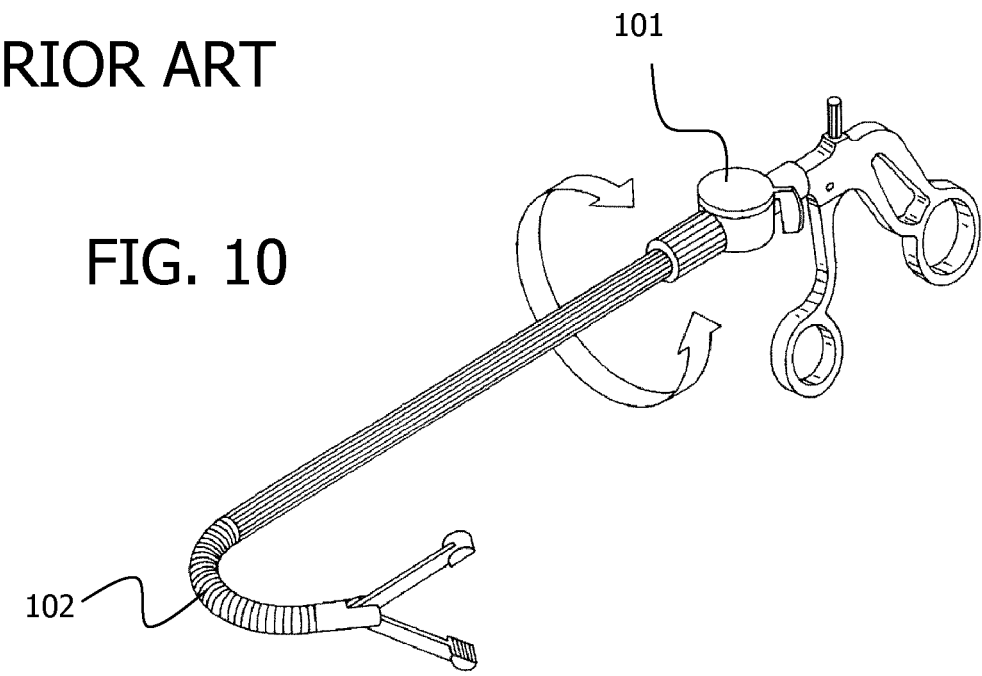
FIG. 10 depicts the prior art configuration of a handle for a bi-directional articulated instruments according to U.S. Pat. No. 5,766,196. When it is desired to change the position of the bendable section 102 from straight to bent or vice versa, the lever 101 is moved 90 degrees which rotates the rotor to move the control wires.
Figure 11:
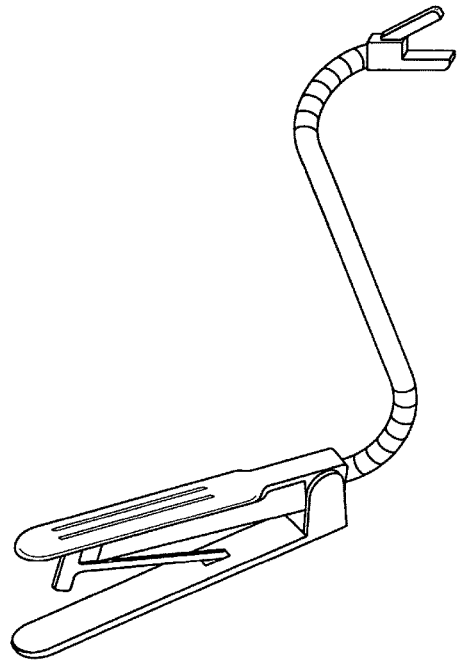
FIG. 11 depicts the prior art configuration of a traditional in-line handle for omni-directional articulated instruments according to U.S. Pat. No. 7,410,483.
Figure 12:
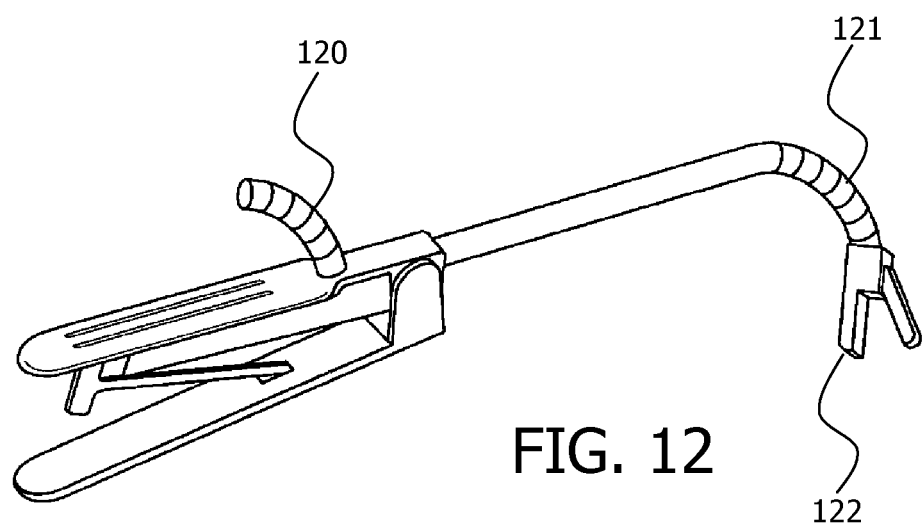
FIG. 12 depicts the prior art configuration of an omni-directional articulated instrument in which the proximal link set 120 is separately manipulated in order to steer distal end tool 122, similar to a joystick, according to U.S. Pat. No. 7,410,483. Proximal link set 120 is operably connected to distal link set 121. The link cables are routed such that link set 120 emerges from the handle itself with the distal-most link of the link set being secured to handle.
Figure 13:
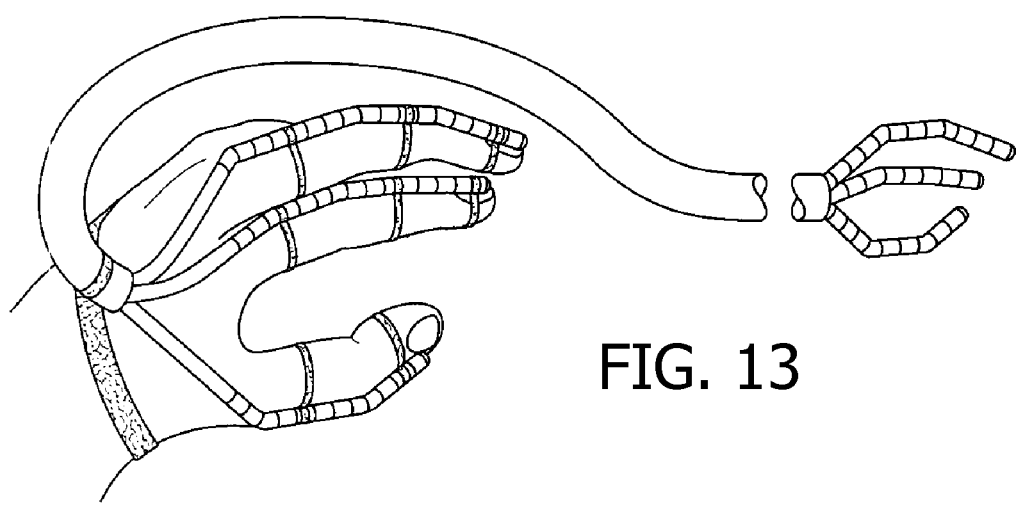
FIG. 13 depicts the prior art configuration of a device that not only provides a hand user interface, but an actuation mechanism that allow for close simulation of human hand movements to enhance remote maneuverability, according to U.S. Pat. No. 7,410,483. A plurality of articulating mechanism may also be combined in such a way that a users finger movement can be remotely mimicked to manipulate an object or body tissue
Figure 16:
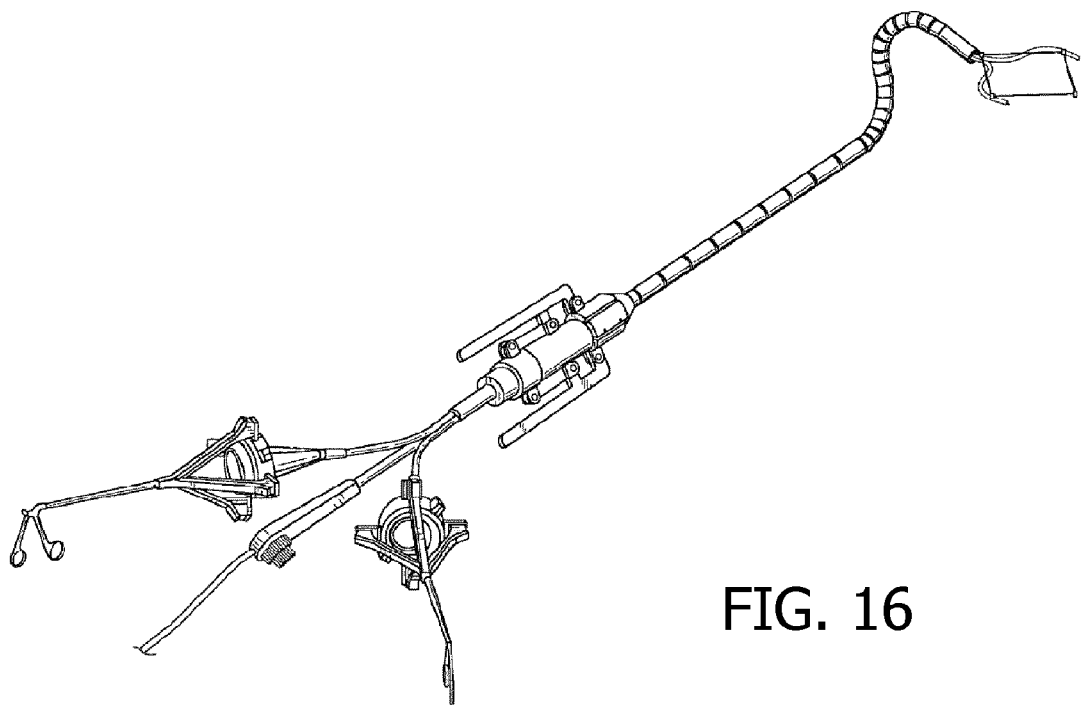
FIG. 16 depicts the prior art configuration of a traditional pistol-grip handle for omni-directional articulated instruments according to U.S. Pat. No. 7,833,156. The configuration allows for intra-abdominal triangulation through a single incision.

One embodiment of the invention is bodily-invasive steerable device (100), in particular, an endoscopic device (100) having a proximal (201) and distal (205) end comprising a:
  steering mechanism (50) having a proximal bending part (202), a distal bending part (204), and an intermediate part (203) disposed between the proximal bending part (202) and the distal bending part (204) configured mechanically to transmit forces applied at the proximal end (201) to the distal end (205). The steering mechanism configured such that the distal bending part (204) moves responsive to movements of the proximal bending part (202),
  a handle (206) coupled to the proximal bending part (202) to effect manual bending; wherein the handle (206) comprises at least one grip member (210) that extends distally (205), at least over the proximal terminal end (171) of the proximal bending part (202).

The distal bending part (204) may be configured for movement in at least two different intersecting planes. The proximal bending part (202) may be configured for movement in at least two different intersecting planes. The handle (206) may comprise two grip members (210), one configured to engage a thumb of a hand, the other configured to engage a finger of the same hand, said grip members arranged to maintain an open palm of the hand. There may be two grip members each disposed with ring or annular segment configured to engage a digit, wherein one or both grip members (210) are levers, and the position of the one or both levers is not biased.

Another embodiment of the invention is an endoscopic device (100) as described above wherein the steering mechanism (50) is configured for omni-directional movement of the distal end.

Another embodiment of the invention is an endoscopic device (100) as described above wherein the terminal distal end (170) of at least one grip member (210) in a native straight configuration is at a distance of at least 20 mm from said steering mechanism (50) to prevent collisions with said steering mechanism (50).

Another embodiment of the invention is an endoscopic device (100) as described above wherein the inclination of a plane defined by a grip member (210) relative to the longitudinal axis of the intermediate part (203) of said steering mechanism is between 0° and 75°.

Another embodiment of the invention is an endoscopic device (100) as described above wherein the inclination of a plane defined by a grip member (210) relative to a longitudinal axis of the intermediate part (203) of said steering mechanism is adjustable.

Another embodiment of the invention is an endoscopic device (100) as described above wherein the handle (206) is dismountably fixed to the proximal bending part (202) of said steering mechanism (50).

Another embodiment of the invention is an endoscopic device (100) as described above wherein the handle (206) is rigidly fixed to the proximal bending part (202) of said steering mechanism (50).

Another embodiment of the invention is an endoscopic device (100) as described above wherein the handle (206) is flexibly mounted to the intermediate part (203) of said steering mechanism (50).

Another embodiment of the invention is an endoscopic device (100) as described above wherein the handle (206) comprises a base element (219) for attachment to the proximal bending part (202), and of at least one grip member (210).

Another embodiment of the invention is an endoscopic device (100) as described above wherein the base plate is fixed to proximal bending part of said steering mechanism according an angle between 0° and 85°.

The handle (206) may be lockably rotatable relative to the proximal bending part (202). The device (100) may be further provided with an end effector at the distal end of the distal bending part (204) wherein the steering mechanism

(50) is configured such that the end effector is rotationally fixed in relation to the distal bending part (204), and the end effector is rotatable when the distal bending part (204) is in a bent position, by a complementary rotation of the proximal bending part (202). The device (100) may be comprised in an endoscope, videoscope or vascular catheter.

DETAILED DESCRIPTION OF THE INVENTION

Unless defined otherwise, all technical and scientific terms used herein have the same meaning as is commonly understood by one of skill in the art. All publications referenced herein are incorporated by reference thereto. All United States patents and patent applications referenced herein are incorporated by reference herein in their entirety including the drawings.

The terms "distal" and "proximal" are used through the specification, and are terms generally understood in the field to mean towards (proximal) or away (distal) from the surgeon's side of the apparatus. Thus, "proximal" means towards the surgeon's side and, therefore, away from the patient's side. Conversely, "distal" means towards the patient's side and, therefore, away from the surgeon's side.

Reference is made in the description below to the drawings which exemplify particular embodiments of the invention; they are not at all intended to be limiting. It will be understood that the skilled person may adapt the device and substitute components and features according to the common practices of the skilled artisan.

In addition to use in a laparoscopic procedure, the instrument of the present invention may be used in a variety of other diagnostic or therapeutic procedures including, but not limited to neurosurgery, ophthalmic surgery, ENT surgery, thoracic and cardiac surgery, arthroscopy etc. The present invention relates to a steerable device. The steerable device is preferably a bodily invasive medical device. The steerable device may be incorporated into or substantially function as an endoscope, a videoscope, a catheter, in particular an endovascular catheter.

Figure 18:
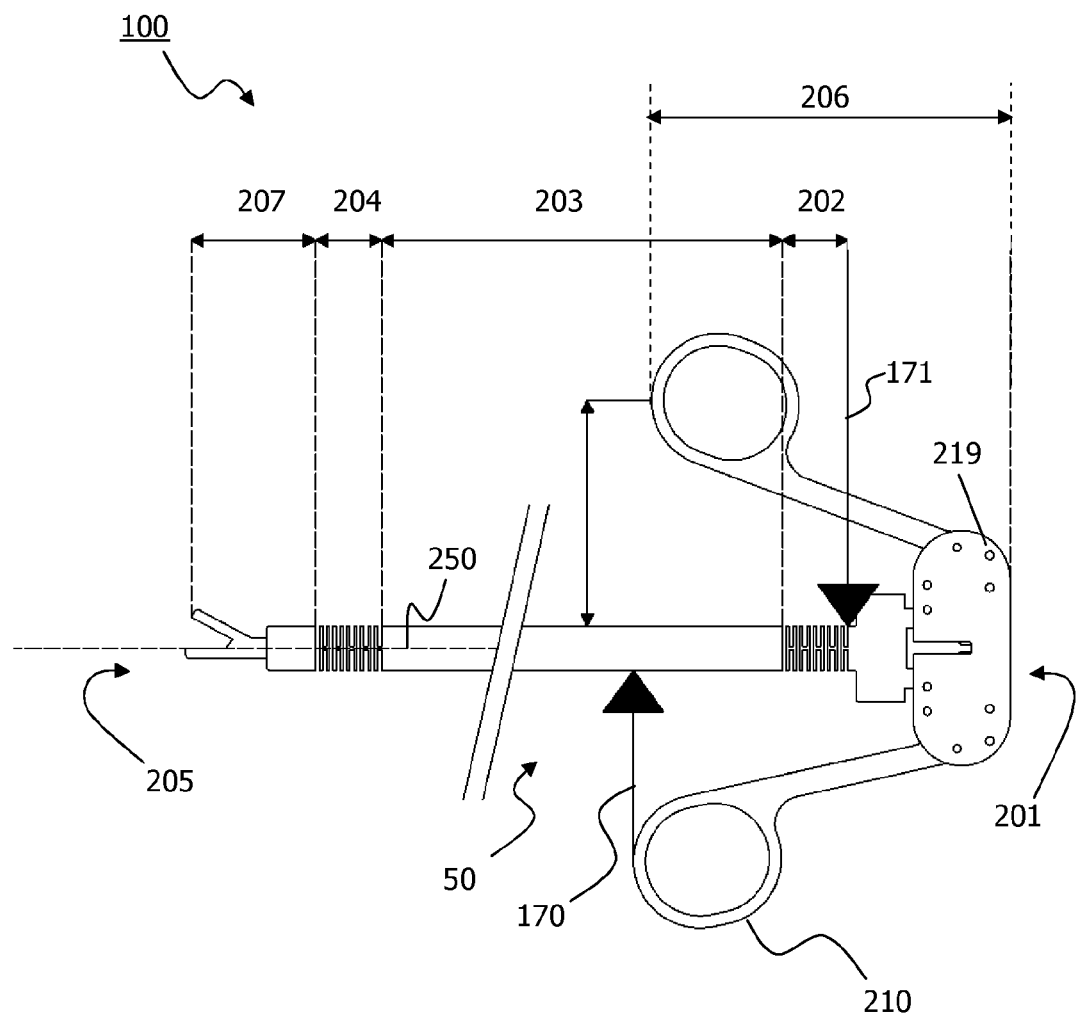
FIG. 18 shows a schematic view of the present invention configuration. Proximal end 201, proximal bending part 202, intermediate part 203, central longitudinal axis 250 of the intermediate part 203, distal bending part 204, distal end 205, distal end piece 207 that may be an end effector or visualization means, handle 206, grip member 210 and base element 219.

With reference to FIG. 18, the steerable device 100 of the invention has a proximal end 201 and a distal 205 end. The steerable device comprises a steering mechanism 50 having a proximal bending part 202, a distal bending part 204, and an intermediate part 203 disposed between the proximal bending part 202 and the distal bending part 204. The proximal bendable part 202 has a proximal 201 end and a distal 205 end, the distal 205 end being adjacent to the intermediate part 203, and the proximal 201 end being adjacent to the handle 206. The distal bendable part 204 similarly has a proximal 201 end and a distal 205 end, the proximal 201 end being adjacent to the intermediate part 203. The distal 205 end of the distal bendable part 204 may be adjacent to a distal end piece 207. The steering mechanism 50 preferably has a circular transverse profile.

The proximal bending part 202 is moved by the user (e.g. the surgeon). The intermediate part 203 is configured mechanically to transmit forces applied at the proximal end 201 to the distal end 205. The steering mechanism 50 is configured such that the distal bending part 204 moves responsive to movements of the proximal bending part 202. Movements of the proximal bending part 202 and the distal bending part 204 are relative to the intermediate part 203. The steerable device further comprises a handle 206 coupled to the proximal bending part 202 to effect manual bending. The handle 206 comprises a grip member 210 that extends distally 205, at least over the proximal terminal end of the proximal bending part 202. The steering mechanism may be configured such that a rotation of the intermediate part 203, (e.g. by rotation of the handle 206) causes a rotation of the distal bendable part 204 around a central axis of the intermediate part 203, even when the distal bendable part 204 is bent.

Figure 20:
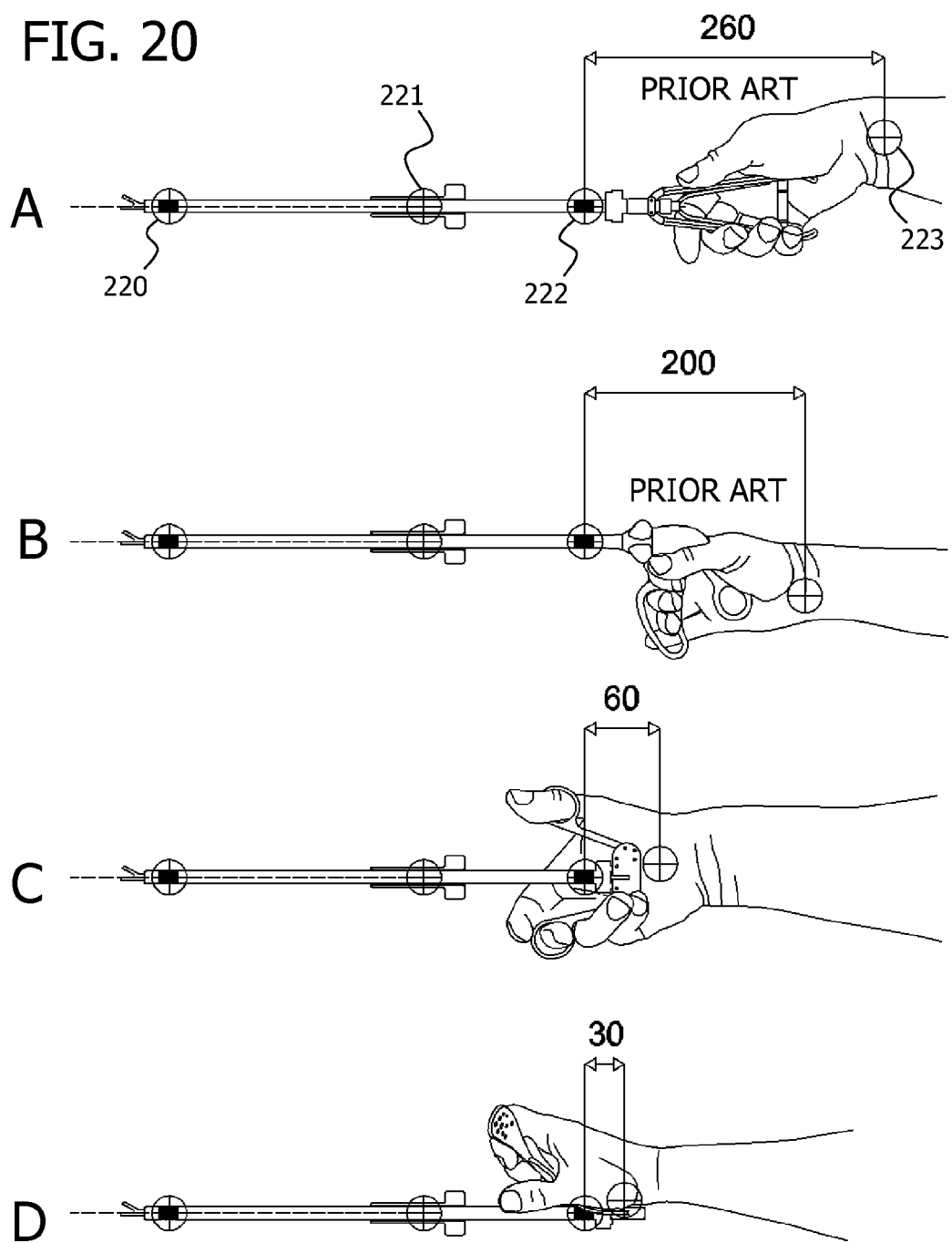
FIG. 20 shows a schematic overview of the distance between the rotation point at the surgeons' wrist 223 and the rotation point at the proximal bending part 222 of the steerable instrument in a prior art configuration A and B and in the present invention configuration C and D.

The inventors have found that the configuration provided by the invention reduces the problem of crosstalk in manually actuated steerable devices, in particular of endoscopes. The reason for this crosstalk is the non-coinciding of the rotation point of the proximal bending part 222 and the rotation point of the operators wrist 223 FIG. 20. In most wrist-controlled, omni-directional articulated instruments using pistol-like, wishbone-like or scissor-like handles, the distance between the two rotation points is relatively large, for instance, more than 200 mm.

Figure 21:
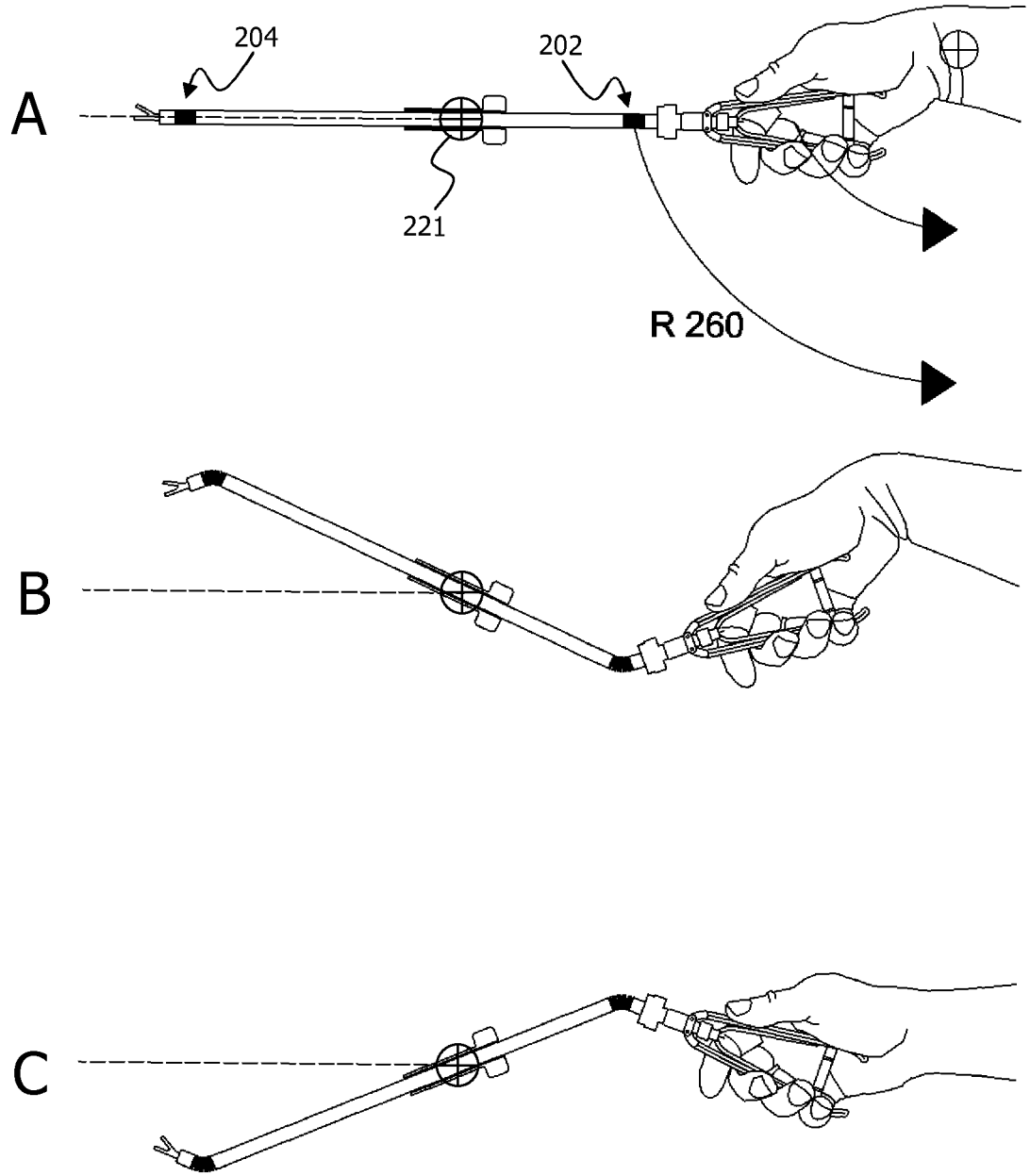
FIG. 21 illustrates the result of crosstalk due to a long distance between the rotation point at the surgeon's wrist and the rotation point at the proximal bending part of the steerable instrument in the prior art configuration of an in-line handle. Bending the proximal part, in order to deflect the tip of the instrument to the left, will result in an additional unintended movement of the whole instrument around its fulcrum point 221 to the right FIG. 21B.

When a surgeon, trying to deflect the instrument's tip, rotates his/her hand around their wrist, the proximal bendable part will also rotate around this wrist with a radius of about 260 mm FIG. 21A. Since the axis of the shaft is determined by the fulcrum point 221 at the level of the trocar in the abdomen and the proximal bendable zone, the whole instrument changes its orientation.

Figure 23:
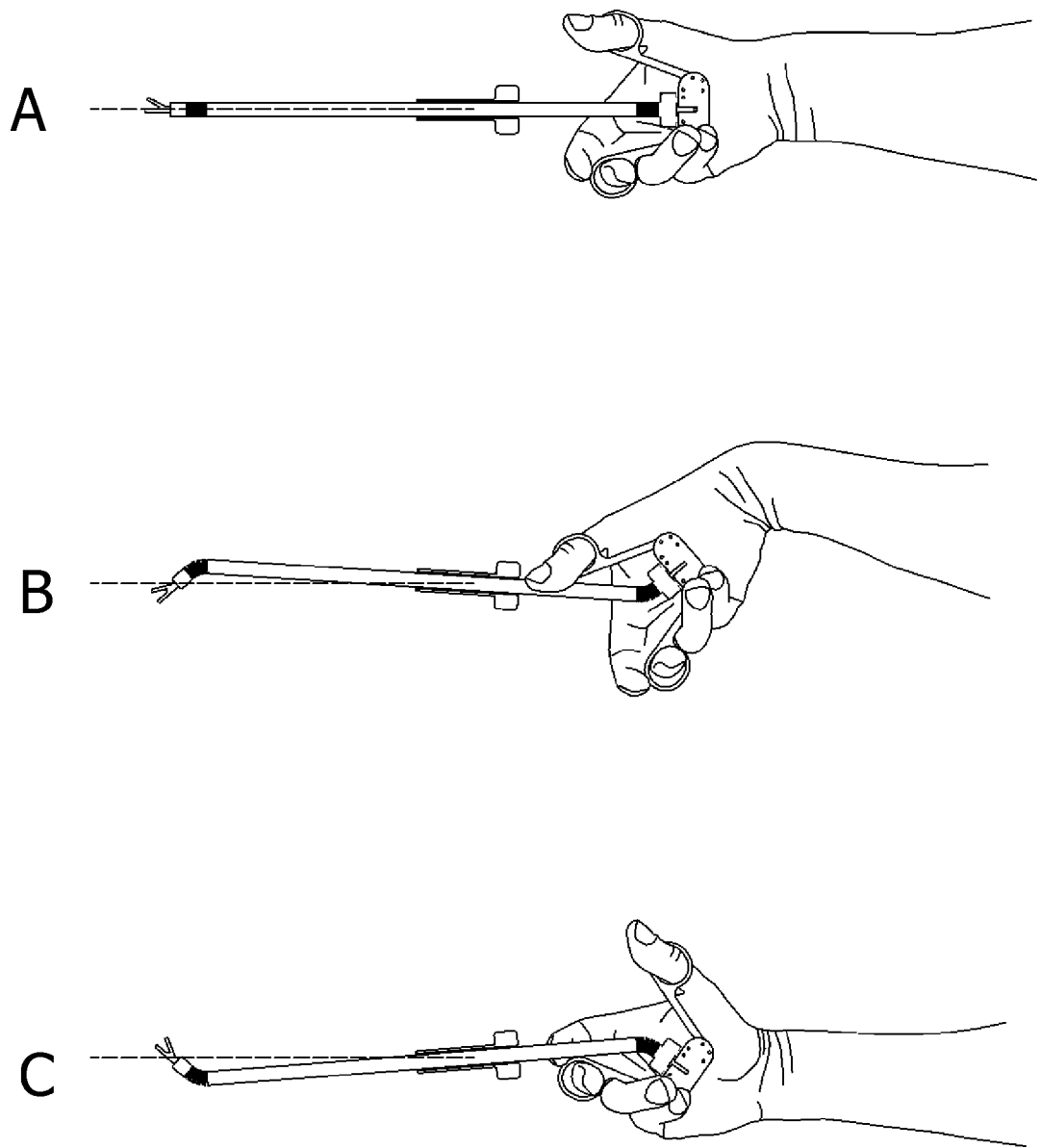
FIG. 23 illustrates reduced crosstalk thanks to a short distance (60 mm) between the rotation point at the surgeons' wrist and the rotation point at the proximal bending part of the steerable instrument in the present invention configuration.

In the present invention this distance can be reduced. Using the configuration in FIG. 20C, for instance, the distance can be reduced to around 60 mm, resulting in a significant reduction FIG. 23 of crosstalk effect exhibited in the prior art FIGS. 21 and 22. In an alternative embodiment the distance may be reduced to even less than 30 mm FIG. 20D resulting in a further reduction still. The effect can be attributable to the handle of which the grip member 210 extends distally over the proximal bending part 202, more preferably, extends distally over the proximal terminal end of the proximal bending part 202.

To prevent collisions between the grip member 210 and the proximal bending part 202 or intermediate part 203 of the steering mechanism, the grip member 210 may divert away from the central longitudinal axis of the steering mechanism.

Using the invention, the grip member 210 of the handle is brought to a position distal to the proximal bendable zone. The goal is to bring the rotation point of the proximal bending part 222 and the rotation point of the surgeon's wrist 223 as close together as possible.

Figure 24:
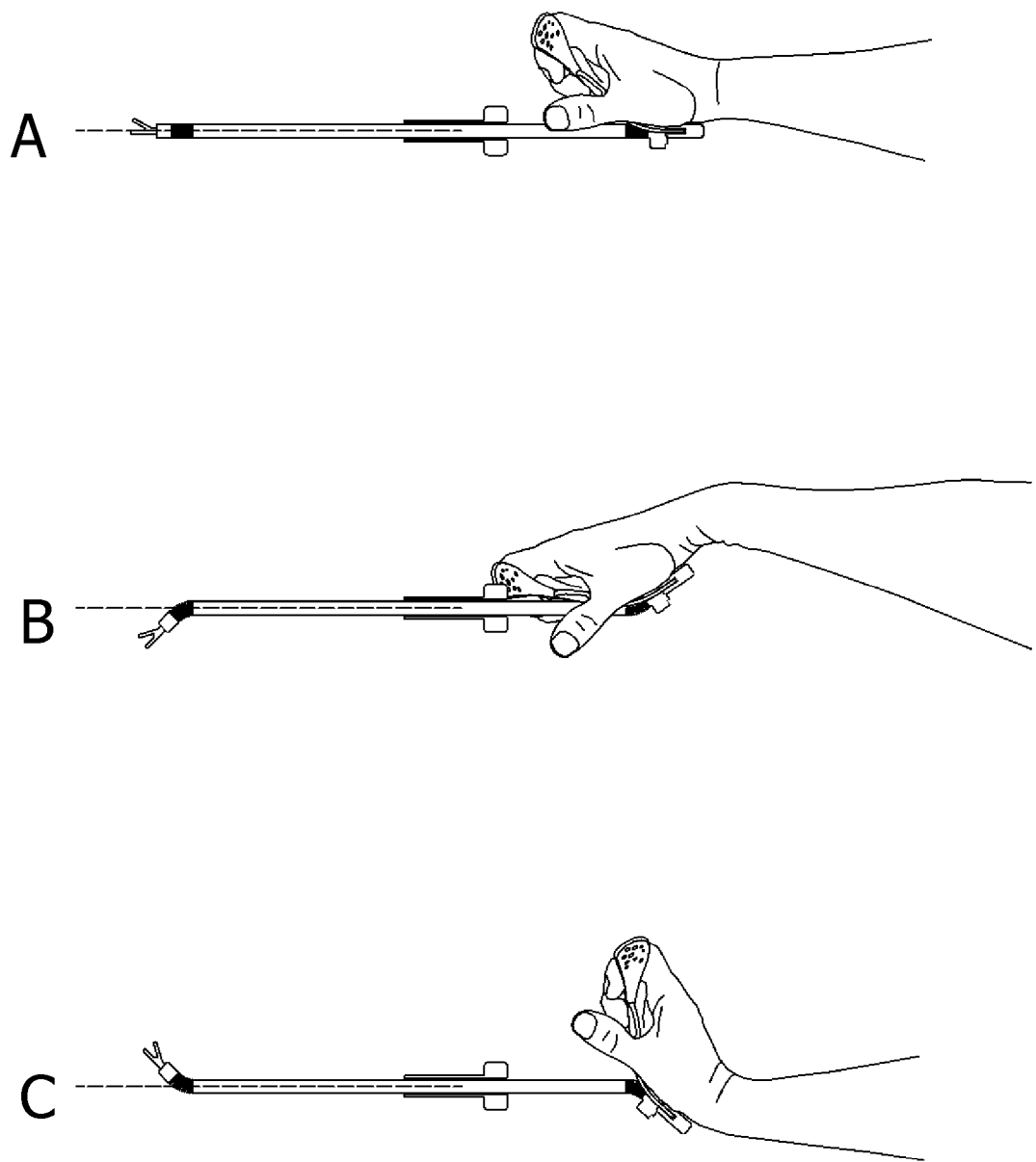
FIG. 24 illustrates reduced crosstalk thanks to a short distance (30 mm) between the rotation point at the surgeons' wrist and the rotation point at the proximal bending part of the steerable instrument in the present invention configuration.

An interesting observation is that a very small amount of crosstalk might be advantageous. As can be appreciated from FIG. 23A to C the swinging of the whole instrument around the fulcrum over a small angulation has the benefit that the jaws of the distal actuating tip circulate around the same operative spot. It is a compensation for the length of the distal tip. This becomes more clear when comparing with FIG. 24A to C an embodiment in which crosstalk is virtually absent. Here it can be appreciated that the jaws of the distal actuating tip overshoots the operative spot. As mentioned earlier, the handle 206 coupled to the proximal bending part 202, comprises a grip member 210 that extends in a distal direction over at least over the proximal terminal end of the proximal bending part 202. In particular, the extension in the distal direction is considered when the proximal bending part 202 is in a neutral (unbent) configuration.

There may be one grip member, or more than one grip member (e.g. 2, 3, 4 or more). When there are two grip members, they may be arranged diametrically around a central longitudinal axis of the proximal bending part 202.

A grip member 210 may comprise a member, that is preferably longitudinal, having a proximal and distal end, the proximal end being attached to the proximal bending part. The distal end may comprise a hook, or ring (open or closed, circular or non-circular (e.g. oval)), or annular segment for a thumb or finger, particularly at the terminal end.

Figure 25:
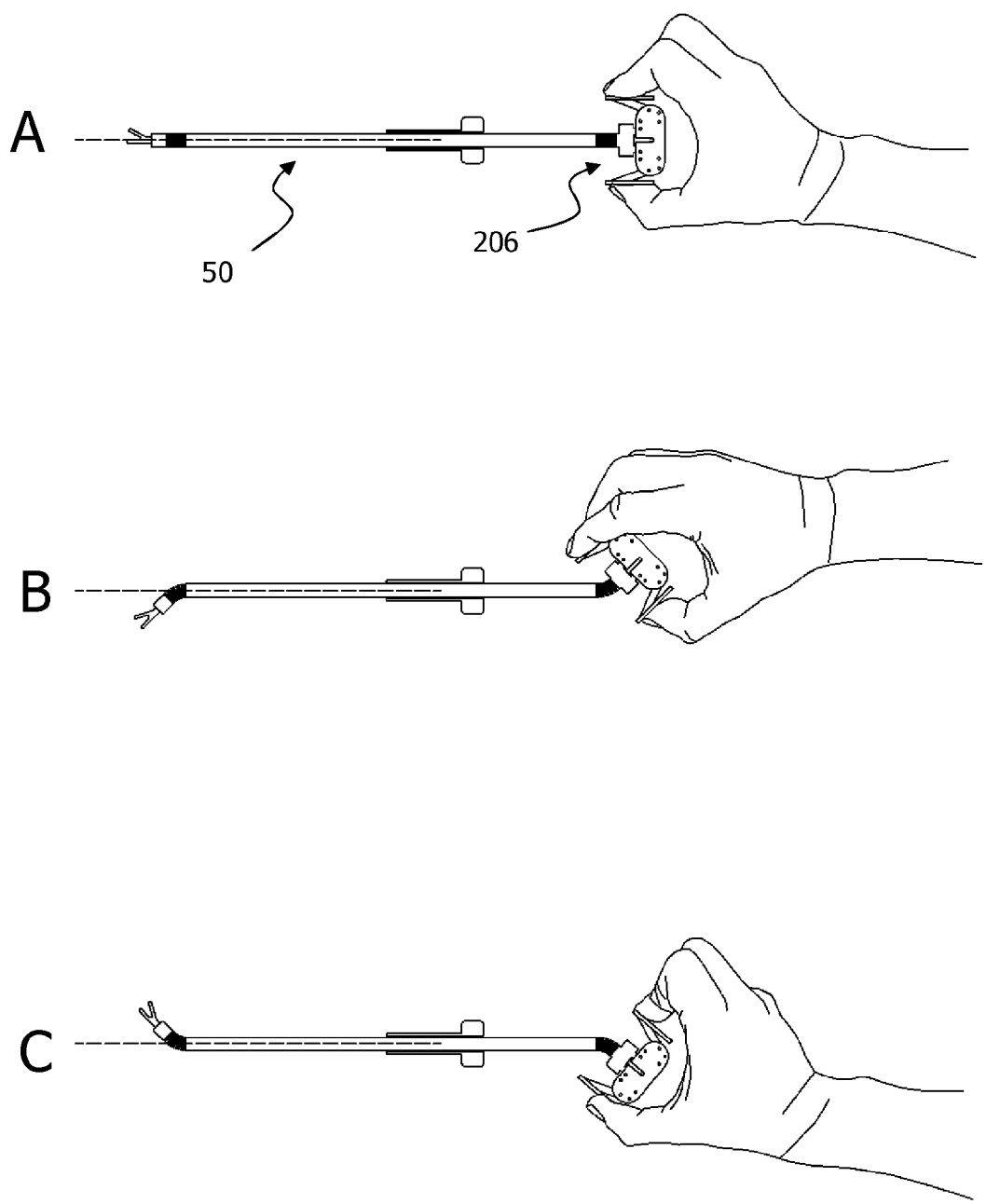
FIG. 25 illustrates an embodiment with reduced crosstalk. Steering of the distal tip is based on wrist and finger movements allowing very precise surgical procedures.

In a preferred configuration, there are two grip members, one for engagement with a thumb, and one for engagement with a finger of the same hand. Preferably, the two grip members 210 are configured such that the handle 206 is gripped with the palm open i.e. the handle 206 is gripped by the fingers, and not through clenching with the palm. In such configuration, the grip members 210 may be positioned either side of the proximal bending part 202, as shown, for instance, in FIG. 18. The separation between the two grip members 210 forces the hand into an open position. The palm may be placed over the proximal bending part 204. Examples of the grip members placed to maintain the open palm configuration is shown in FIGS. 20C, 20D, 25 A to C. One or both grip members may be levered, for instance, to control a jaw at the distal end.

By using an open palm configuration, not only is the position of the handle 206 controlled by the wrist alone allowing more intuitive control (see FIGS. 23A to C, 24A to C, 25A to C), but the grip allows the user simultaneously to move the proximal bending part 202 omnidirectionally and operate any levered grip members. When a closed palm is used to grip the handle, by contrast, omnidirectional control of proximal bending part 202 must temporarily be relinquished when a lever is released since grip on the handle must be released at the same time.

The handle may further comprise a base element 219 to which the grip member 210 is attached, which base element 219 contains a coupling for attachment to the proximal bending part 202. The grip member may be rigidly attached to the base element 219. Alternatively, the grip member 210 may be pivoted with respect to the base element 219, to act as a lever actuator for a tool such as a grip tool, disposed at the distal end of the device.

Figure 17:
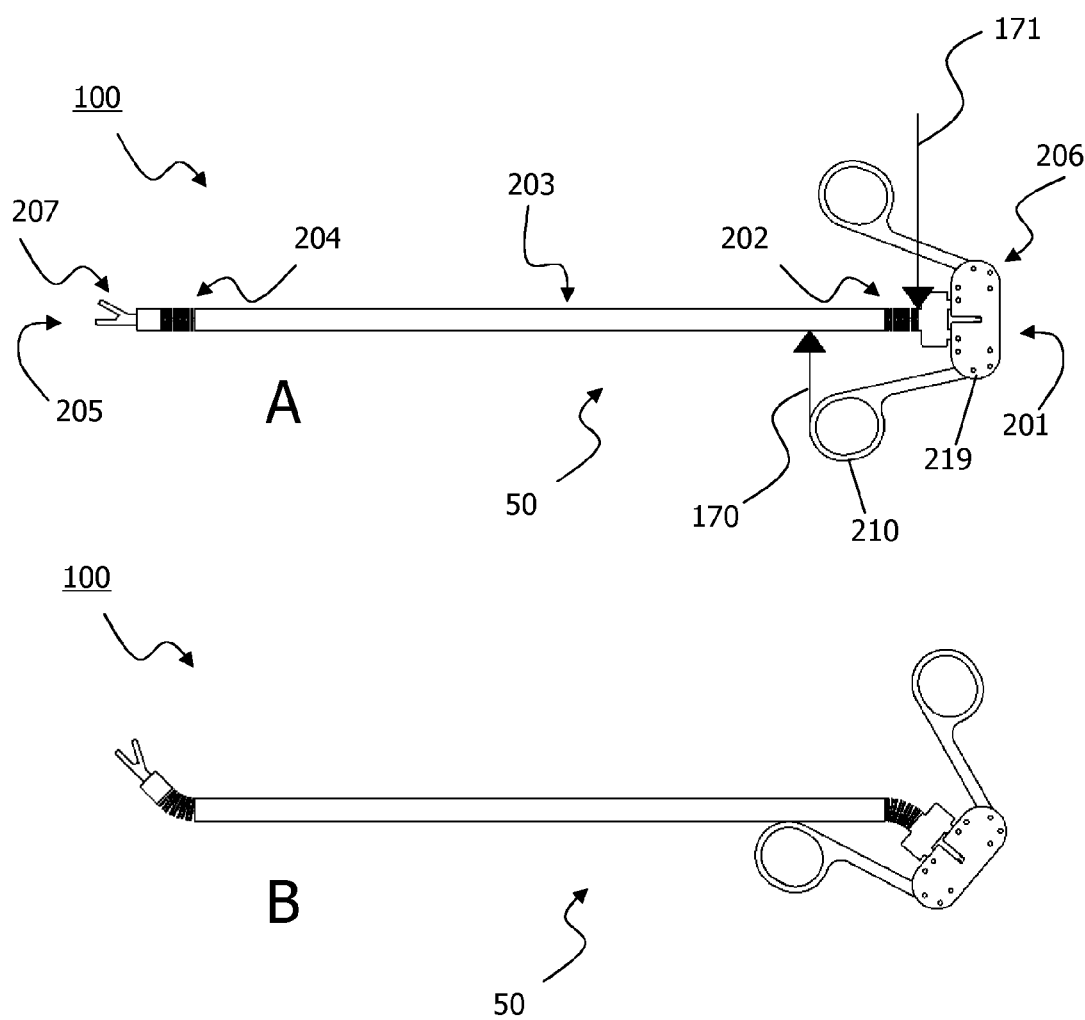
FIG. 17 depicts the present invention configuration in native (straight, unbent) A and bent B position. The long arrows 170, 171 indicate the distal most end 170 of the distally extending grip member 210 (in relation to its pivoting point) and the proximal terminal end 171 of the proximal bending part 202.

From FIG. 17 and FIG. 18 it can be appreciated that a diverging of the grip member 210 away from the central longitudinal axis of the intermediate part 203 is advantageous. When bending the proximal part 202 in order to steer the distal tip 205, a collision between the grip member 210 and the intermediate part 203 of the steering mechanism is avoided. It is envisaged that other collision avoiding configurations are possible.

A far lateral positioning of pivot point 215, when the grip member 210 is pivoted, even with converging levers will have the same positive result. In another embodiment (FIG. 24) conflict avoidance between the grip member 210 and intermediate part 203 is achieved by an inclination of the plane defined by grip member 210 relative to the longitudinal axis of the intermediate part of the steering mechanism in a straight position of the distal effector. It can be appreciated from FIG. 24B that a downward movement of the handle until 45 degrees is possible without conflict. Upward movement and left-right movements are completely free of interaction with the intermediate part.

Figure 19:
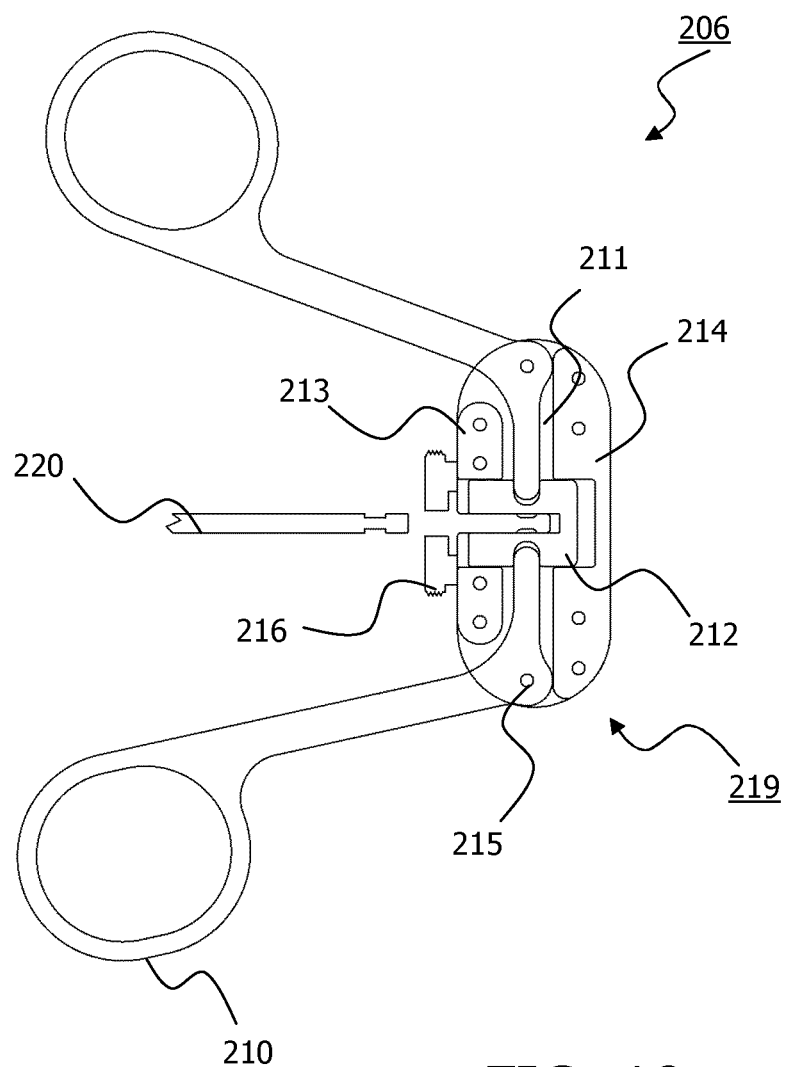
FIG. 19 depicts in detail the inside mechanism of the handle transferring the rotational movement of the grip members 210 to a linear motion of the actuating rod 220.

The handle 206 may be coupled to the proximal bending part 202 of the steering mechanism by a threaded annular fixation plate 216 (FIG. 19) in the base of the handle. The annular fixation plate 216 is connected to the base plate 211. The cover plate has been omitted in order to have a better understanding of the inside. The proximal end of the push/pull rod 220 is coupled to the grip members 210, which act as levers, by an intermediate linear sliding plate 212. In FIG. 19 this rod is removed from the handle and shifted to the left. The intermediate plate 212 is slidably mounted. It is maintained by bearing plates 213 and 214. When a surgeon grasps the handles in order to close the jaws of the end effector a rotation of the grip member 210 around pivot point 215 induces a linear proximal ward motion in the intermediate sliding plate 212. It is commonly understood by one of skill in the art that other mechanisms to translate a pivotal movement of levers to an actuation at the distal tip are known e.g. ball coupling.

Some embodiments may contain only one pivoting grip member (i.e. that acts as a lever) and one static grip member. Embodiments that do not require actuation at the tip e.g. a videoscope can be constructed with only one or two grips extending distally from the proximal portion of the proximal bending part 171.

In one embodiment, there are two grip members, wherein one or both are levers that are biased in an open configuration, using a compliant member. In another embodiment, there are two grip members, wherein one or both grip members are levers and the position of one or both levers is not biased. When one or both grip members are levers and the position of one or both levers is not biased, the surgeon can readily apply force in both the closing and opening actions of the levers. This is particularly suitable when the distal end of the grip member comprise a hook, or ring (open or closed, circular or non-circular (e.g. oval)), or annular segment for a thumb or finger. An electrical, electronic or mechanical switch may be disposed on the handle to control another device. For instance, an electrical push button may control a laser or electrocautery.

The fixation plate may be disposed with a ferrule or rotating ring that allows the push/pull rod and steering mechanism to rotate around its own axis relative to the handle. In this way the jaws of the distal actuator can be rotated.

Optionally, the handle may be provided with a locking mechanism to fix the proximal bending part in a desired position.

Optionally, the handle may be provided with a ratcheting or self-locking clutch mechanism to fix or prevent opening of a jaw tool at the distal end. A quick-release system may be provided to release the jaws.

In another embodiment, the grip member 210 may be a shortened, to allow steering with the tips of the fingers or thumb, as shown for instance in FIGS. 25A to C. This allows for finger dexterity. The movements of the proximal part are a result of wrist movements and finger movements. This is especially of interest in very precise procedures such as suturing of micro anastomosis of blood vessels in cardiac surgery.

Figure 26:
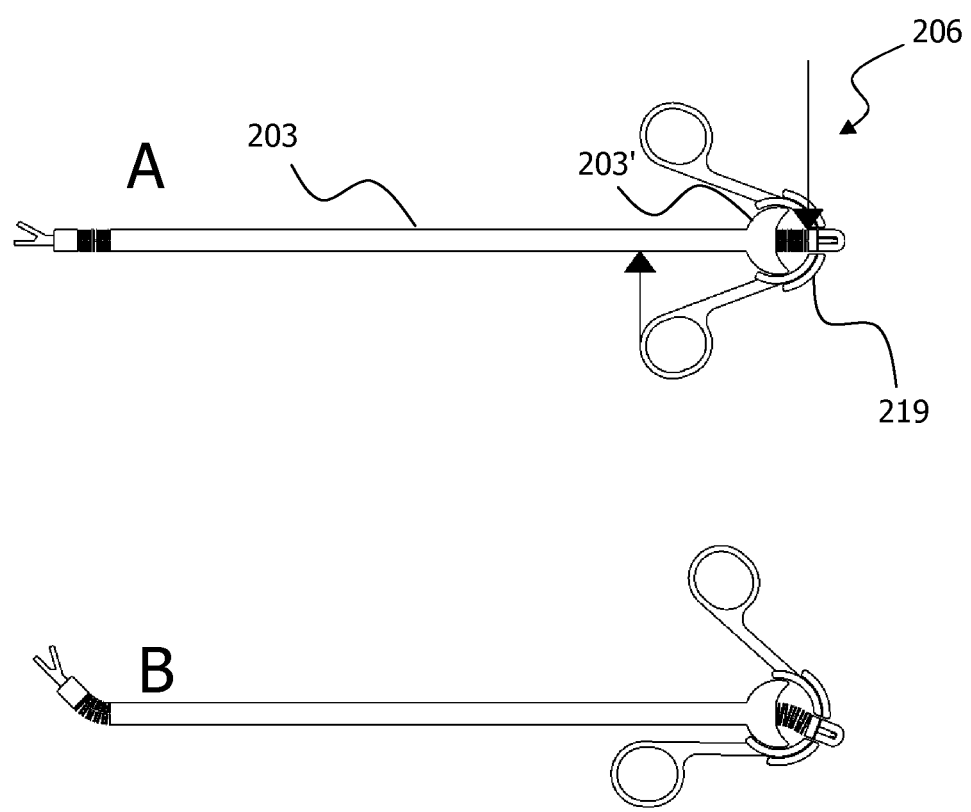
FIG. 26 depicts the present invention configuration in native straight A and bent B position. The long arrows indicate the distal most end of the distally extending grip member and the proximal most end of the proximal bending part.

In another embodiment, the base element 219 comprises one half of a ball and socket joint, to which the grip member 210 is attached and which couples to the proximal bending part 202. The other half 203' of the ball and socket joint is attached to the proximal end of the intermediate part 203. An example of this configuration is shown in FIGS. 26A and B.

The steerable device may be formed mostly from stainless steel, titanium or injection molded plastic, or a mixture of one or more these. The handle is preferably formed from stainless steel, titanium or injection molded plastic, or a mixture of one or more these.

The handle 206 may be rotatable, preferably lockably rotatable, relative to the proximal bending part 202. The handle 206 may be revolute connection, preferably lockable revolute connection, with the proximal bending part 202. The handle 206 may be rotatable relative to or in revolute connection with the proximal bending part 202 around one axis. This allows the operator to reset the position of an end effector (e.g. a jaw) relative to the handle 206.

The handle may further be provided with a disengagable locking mechanism, configured to lock the revolute position of the handle 206 relative to the proximal bending part 202. The disengagable locking mechanism may be activated by a button on the handle 206. The disengagable locking mechanism may comprise a lockable collar.

The steering mechanism 50 of the invention is preferably an omnidirectional articulated instrument which is known in the art. It has a proximal 201 and distal end 205, a proximal 202 and distal 204 bending part and an intermediate part 203 in between (FIG. 18). Movement of the proximal end 201 is transferred to a movement at the distal end 205. The resulting directional movement of the distal end can be inverted, mirrored or otherwise depending on the degree of rotation. In FIG. 18 the instrument is shown with a break between proximal end and the distal end.

Omni-directional steering mechanism 50 may bend in any direction (about 360°). Omni-directional steering mechanism 50 may bend in at least 2, 3, 4, 5, 6, 7, 8, 9, 19, 11 or 12 different directions.

Figure 27:
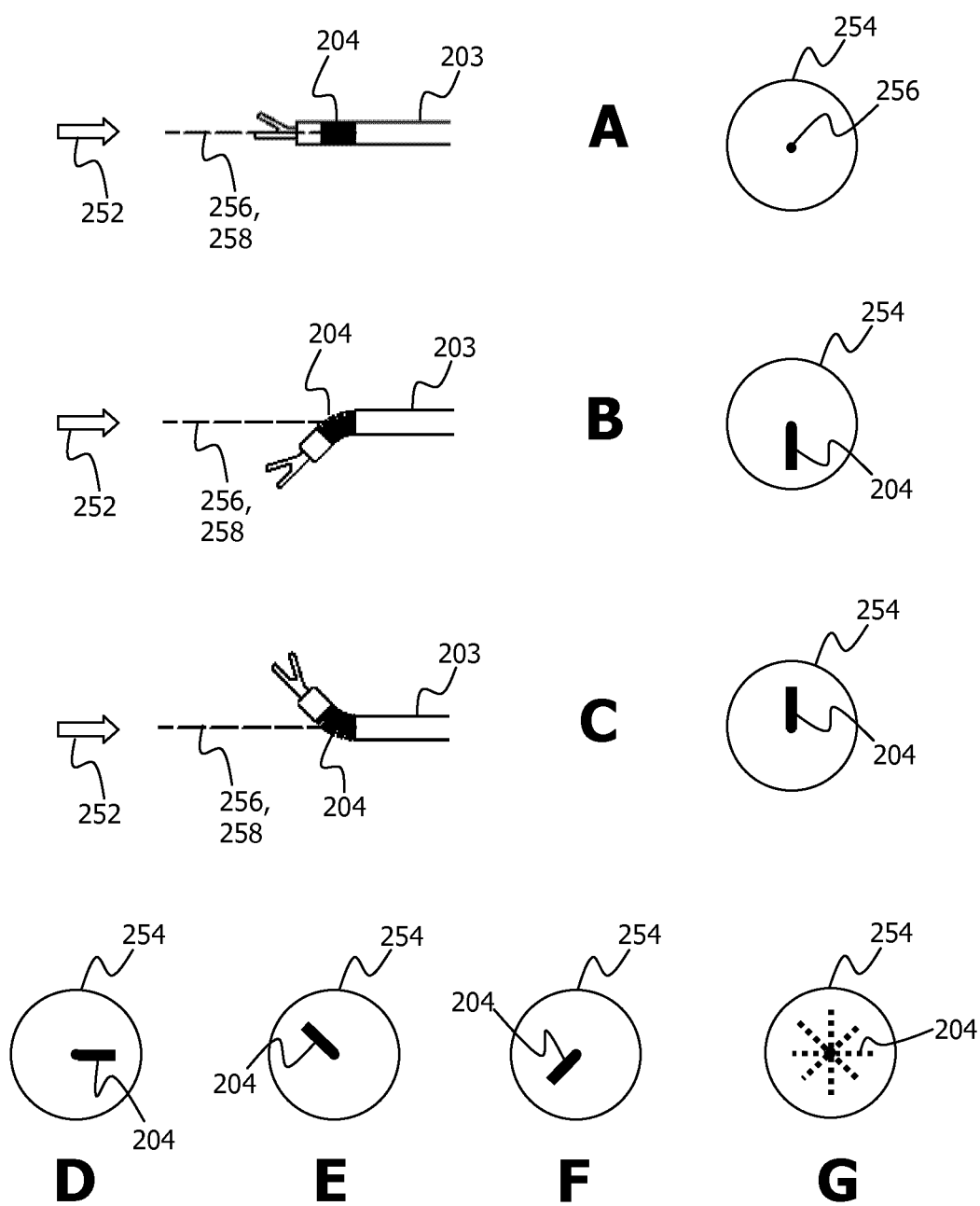
FIGS. 27A to G depict the distal bending part bent in a plurality of different directions relative to a radial axis.

Omni-directional steering mechanism 50 may be configured to bend the distal bending part 204, relative to the intermediate part 203, in any radial direction (e.g. at least 2, 3, 4 5, 6, 7, 8, 9, 10, 11, or 12 or more different radial directions). The radial direction may be with respect to a radial axis 258 (FIG. 27). The radial axis 258 may be co-axial with the central longitudinal axis 250 of the intermediate part 203. The radial axis 258 may be co-axial with a central longitudinal axis 250 of the distal end 205 of the intermediate part 203. The radial axis 258 may be co-axial with a central longitudinal axis of the distal bending part 204 when adopting a linear form. The radial axis 258 may be co-axial with a central longitudinal axis 256 of the proximal end 201 of the distal bending part 204.

Examples of different radial directions are depicted in FIG. 25 A to G. In FIG. 25A, the distal bending part 204, is unbent, and the projection 254 viewed along the radial axis 258 in the direction of the arrow 252 shows no radial movement of the distal bending part 204. In FIG. 25B, the distal bending part 204 is bent downwards relative to the intermediate part 203, and the projection 254 viewed along the radial axis 258 in the direction of the arrow 252 shows a radial movement of the distal bending part 204 in the "6h00" direction. In FIG. 25C, the distal bending part 204 is bent upwards relative to the intermediate part 203, and the projection 254 viewed along the radial axis 258 in the direction of the arrow 252 shows a radial movement of the distal bending part 204 in the "12h00" direction. FIGS. 25D, E and F each depict radial movement of the distal bending part 204 in the "3h00", "10h30" and "7h30" directions respectively. FIG. 25G, shows a superimposition of 8 different directions.

The distal bending part 204 may be configured for movement in at least two different intersecting planes. The different planes preferably intersect each other along a common straight line (known as a plane axis herein). The plane axis may be co-axial with a central longitudinal axis 250 of the intermediate part 203. The plane axis may be co-axial with a central longitudinal axis of the distal end of the intermediate part 203. The plane axis may be co-axial with a central longitudinal axis of the distal bending part 204 when adopting a linear form. The plane axis may be co-axial with a central longitudinal axis 256 of the proximal end of the distal bending part 204. The distal bending part 204 may be configured for movement in at least two different planes disposed parallel to and contacting a central longitudinal axis 250 of the intermediate part 203. Two planes are preferably perpendicular to each other.

The distal bending part 204 may be configured for movement in at least 2, 3, 4, 5, 6, 7, 8, 9 or 10 different planes. Said planes are preferably arranged in a star configuration. Preferably, the distal bending part 204 is configured for movement in an infinite number of different planes. The movement is relative to a central longitudinal axis 250 the intermediate part 203.

The distal bending part 204 may be configured for movement, relative to the intermediate part 203, around x- and y-axes, which axes are perpendicular to each other and also perpendicular with respect to the central longitudinal axis (z-axis) of the intermediate part 203.

The distal bending part 204 may be configured for pitch and yaw movement, relative to the intermediate part 203, whereby rotations of the intermediate part 203 represent roll.

The distal bending part 204 may be configured for movement having 2 rotational degrees of freedom that are perpendicular with respect to each other, and perpendicular with respect to the central longitudinal axis of the intermediate part 203.

Furthermore it may be possible to rotate the distal tip of the instrument about its own axis even in a bent status.

With respect to the proximal bending part, the omni-directional steering mechanism 50 may be configured such that the proximal bending part 202, is bendable relative to the intermediate part 203, in any radial direction (e.g. at least 2, 3, 4, 5, 6, 7, 8, 9, 10, 11, or 12 or more different radial directions). The radial direction may be with respect to a radial axis. The radial axis may be co-axial with the central longitudinal axis 250 of the intermediate part 203. The radial axis may be co-axial with a central longitudinal axis 250 of the proximal end 205 of the intermediate part 203. The radial axis may be co-axial with a central longitudinal axis of the proximal bending part 202 when adopting a linear form. The radial axis may be co-axial with a central longitudinal axis 256 of the distal end 205 of the proximal bending part 202. The examples of different radial directions of the distal bending part 204 in FIGS. 25 A to G are applicable to proximal bending part 202.

The proximal bending part 202 may be configured for movement in at least two different intersecting planes. The different planes preferably intersect each other along a common straight line (known as a plane axis herein). The plane axis may be co-axial with a central longitudinal axis 250 of the intermediate part 203. The plane axis may be co-axial with a central longitudinal axis of the distal end of the intermediate part 203. The plane axis may be co-axial with a central longitudinal axis of the proximal bending part 202 when adopting a linear form. The plane axis may be co-axial with a central longitudinal axis 256 of the distal end of the proximal bending part 202. The proximal bending part 202 may be configured for movement in at least two different planes disposed parallel to and contacting a central longitudinal axis 250 of the intermediate part 203. Two planes are preferably perpendicular to each other.

The proximal bending part 202 may be configured for movement in at least 2, 3, 4, 5, 6, 7, 8, 9 or 10 different planes. Said planes are preferably arranged in a star configuration. Preferably, the proximal bending part 202 is configured for movement in an infinite number of different planes. The movement is relative to a central longitudinal axis 250 of the intermediate part 203.

The proximal bending part 202 may be configured for movement, relative to the intermediate part 203, around x- and y-axes, which axes are perpendicular to each other and also perpendicular with respect to the central longitudinal axis (z-axis) of the intermediate part 203.

The proximal bending part 202 may be configured for pitch and yaw movement, relative to the intermediate part 203, whereby rotations of the intermediate part 203 represent roll.

The proximal bending part 202 may be configured for movement having 2 rotational degrees of freedom that are perpendicular with respect to each other, and perpendicular with respect to the central longitudinal axis of the intermediate part 203.

A proximal bendable part 202 has the same meaning as is commonly understood by one of skill in the art. For avoidance of doubt, proximal bendable parts based on flexing of wires or strips, gear mechanisms, ball and socket joints, uncompressible drive rods, lever mechanisms, tubular member with longitudinal cuts, hydraulically or electrically actuated articulation joints, pivotal joints . . . etc are covered by the term proximal bendable part. The same applies mutatis mutandis to a distal bendable part 204.

The device 100 described herein is primarily for laparoscopic or endoscopic procedures. However, it is to be understood that the instrument of the present invention can be used for a wide variety of other procedures, including endovascular procedures, fine mechanical processes etc.

The diameter of the intermediate part 203 may range from about 0.3 mm to about 20 mm or more depending on the application. For endoscopic applications, diameters may range from about 1 mm to about 4 mm for small endoscopic instruments, and about 5 to 20 mm for large endoscopic instruments. For endovascular catheter application, the diameter may range from about 0.3 mm to about 9 mm.

The amplitude of bending motion at the distal bendable part 204 is related in part to the dimensions of the proximal bendable part. Mostly the diameter at the proximal bendable part 202 is larger than the diameter at the distal bendable part 204. The increase in diameter may be linear from proximal to distal or concentrated over a short conical part located at the proximal side of the instrument.

Overall length of the steering mechanism 50 may vary from 6 cm for small endoscopic applications to 200 cm and more for endovascular catheter applications.

The intermediate part 203 in endoscopic surgery may be mostly rigid. However in some situations semi-rigid or flexible configurations may be advantageous. For example, in Single Port Surgery a flexible articulated instruments could be introduced in a prebent guiding tube. This will compensate for the lack of triangulation.

The intermediate part 203 may be straight or (pre)bent.

An end effector or visualization means may be coupled to the distal 205 end of the steering mechanism i.e. to the distal terminal end of the distal bending part 204. Such end effector or visualization is depicted in the figures as a distal end piece 207. End effectors compromise of, but are not limited to, scissors, graspers, clamps, dissectors, ultrasound visualization devices, energy device using ultrasound, drills, electrocautery tips, staplers, lasers, cameras, stapler clip appliers, needle drivers, suction/irrigation channels etc.

The end effector may be rotatable. Preferably, it is rotatable relative to the distal bending part 204. The device may further comprise a rotary actuator at the proximal end 201 of the device and the rotatable end effector at the distal end 205 of the device 100, wherein the steering mechanism 50 is further configured to rotate the end effector responsive to the application of torque to the rotary actuator. The intermediate part 203 may be configured to mechanically transmit the torque applied to the rotary actuator to the rotatable end effector. The rotary actuator may be a turning knob disposed on the handle 206. The rotary actuator may be the handle configured to rotate relative to the proximal bending part 202. Using this arrangement, the end effector may be rotated about its own axis when the distal bending part 204 is bent. The rotatable end effector may be implemented using known means, for instance, using a cylindrical transmission cable. Such elements are described also in US 2009/0192521 for instance. The handle may further be provided with a disengagable locking mechanism, configured to fix the revolute position of the rotary actuator and/or the revolute position of the rotatable end effector. The disengagable locking mechanism may be activated by a button on the handle 206.

The steering mechanism may be configured such that the end effector is rotationally fixed in relation to the distal bending part 204, and the end effector is rotatable when the distal bending part 204 is in a bent position, by a complementary rotation of the proximal bending part 202. Such a mechanism does not require a separate rotary actuator described above. In another embodiment (videoscope) the distal end is provided by a visualization means such as a chip on tip camera (2D or 3D) or optical fibers. The handle with fixed grips according the present invention allows intuitive maneuvering of the camera to allow visual inspection of the operative field. Especially in Single Port Surgery it adds to the avoid clashing with the endoscopic instruments.

The invention claimed is:

1. A bodily-invasive steerable device (100) having a proximal and distal end comprising:
   i) a steering mechanism having
      a proximal bending part,
      a distal bending part, and
      an intermediate part disposed between the proximal bending part and the distal bending part configured mechanically to transmit forces applied at the proximal end to the distal end,
      the steering mechanism configured such that the distal bending part moves responsive to movements of the proximal bending part, and
   ii) a handle coupled to the proximal bending part to effect manual bending; wherein
      the handle comprises at least one grip member that extends distally, at least over the proximal terminal end of the proximal bending part,
      the handle is provided in fixed or lockable axial rotation with respect to the proximal end of the proximal bending part,
      the distal bending part is configured for movement in at least two different intersecting planes, and
      the device is further provided with an end effector at the distal end of the distal bending part, wherein the steering mechanism is configured such that the end effector is rotationally fixed in relation to the distal bending part, and the end effector is rotatable when the distal bending part (204) is in a bent position, by a complementary rotation of the handle.

2. The device according to claim 1 wherein proximal bending part is configured for movement in at least two different intersecting planes.

3. The device according to claim 1, wherein the handle (206) comprises two grip members, one configured to engage a thumb of a hand, the other configured to engage a finger of the same hand, said grip members arranged to maintain an open palm of the hand.

4. The device according to claim 1, wherein there are two grip members each disposed with ring or annular segment to engage a digit, wherein one or both grip members are levers, and the position of the one or both levers is not biased.

5. The device according to claim 1, wherein the terminal distal end of at least one grip member in a native straight configuration is at a distance of at least 20 mm from said steering mechanism to prevent collisions with said steering mechanism.

6. The device according to claim 1, wherein the inclination of a plane defined by a grip member relative to the longitudinal axis of the intermediate part of said steering mechanism is between 0° and 75°.

7. The device according to claim 1, wherein the inclination of a plane defined by a grip member relative to a longitudinal axis of the intermediate part of said steering mechanism is adjustable.

8. The device according to claim 1, wherein the handle is dismountably fixed to the proximal bending part of said steering mechanism.

9. The device according to claim 1, wherein the handle comprises a base element for attachment to the proximal bending part, and of at least one grip member.

10. The device according to claim 1, wherein a base plate is fixed to proximal bending part of said steering mechanism according an angle between 0° and 85°.

11. The device according to claim 1, comprised in an endoscope, videoscope or vascular catheter.

* * * * *